United States Patent
Webster et al.

(10) Patent No.: US 6,465,679 B2
(45) Date of Patent: Oct. 15, 2002

(54) CARBAMATE FUNCTIONAL OLIGOMERS AND COATINGS THEREFROM

(75) Inventors: Dean C. Webster; Allen L. Crain, both of Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 2 days.

(21) Appl. No.: 09/742,332

(22) Filed: Dec. 22, 2000

(65) Prior Publication Data

US 2002/0040110 A1 Apr. 4, 2002

Related U.S. Application Data

(60) Provisional application No. 60/173,557, filed on Dec. 30, 1999.

(51) Int. Cl.⁷ .................... C07C 271/12; C07C 271/06; C07C 271/08; C07C 271/10
(52) U.S. Cl. ................... 560/166; 560/157; 560/160
(58) Field of Search ............................ 560/157, 160, 560/166

(56) References Cited

U.S. PATENT DOCUMENTS

| | | | |
|---|---|---|---|
| 3,852,233 A | 12/1974 | Lindemann | 260/29.6 |
| 4,272,455 A * | 6/1981 | Cook et al. | 564/503 |
| 5,159,098 A | 10/1992 | Plotkin et al. | 558/275 |
| 5,300,328 A | 4/1994 | Rehfuss | 427/388.3 |
| 5,336,566 A | 8/1994 | Rehfuss | 428/524 |
| 5,356,669 A | 10/1994 | Rehfuss et al. | 427/407.1 |
| 5,373,069 A | 12/1994 | Rehfuss et al. | 525/456 |
| 5,474,811 A | 12/1995 | Rehfuss et al. | 427/407.1 |
| 5,512,639 A | 4/1996 | Rehfuss et al. | 525/456 |
| 5,605,965 A | 2/1997 | Rehfuss et al. | 525/100 |
| 5,719,237 A | 2/1998 | Rehfuss et al. | 525/419 |
| 5,726,246 A | 3/1998 | Rehfuss et al. | 525/100 |
| 5,756,213 A | 5/1998 | Ohrbom et al. | 428/412 |
| 5,760,127 A | 6/1998 | Bammel et al. | 524/590 |
| 5,766,769 A | 6/1998 | Ohrbom et al. | 428/523.1 |
| 5,770,650 A | 6/1998 | McGee et al. | 524/590 |
| 5,792,810 A | 8/1998 | Menovcik et al. | 524/590 |
| 5,912,382 A | 6/1999 | Marquis et al. | 560/166 |

FOREIGN PATENT DOCUMENTS

| | | |
|---|---|---|
| EP | 0 594 142 A1 | 4/1994 |
| EP | 0 661 315 A1 | 7/1995 |
| EP | 0 767 187 A1 | 4/1997 |
| EP | 0 767 226 A1 | 4/1997 |
| EP | 0 767 231 A1 | 4/1997 |
| EP | 0 869 139 A1 | 10/1998 |
| EP | 0 889 103 A2 | 1/1999 |

* cited by examiner

*Primary Examiner*—Gary Geist
*Assistant Examiner*—M. P. Moon
(74) *Attorney, Agent, or Firm*—Morgan, Lewis & Bockius LLP

(57) ABSTRACT

This invention involves a carbamate functional polymer or oligomer made by reacting a cyclic carbonate with ammonia or a primary amine, then reacting the resulting hydroxycarbamate with a polyfunctional material containing groups reactive with hydroxyl groups to form a polyfunctional carbamate. The polymer formed is mixed with an aminoplast, coated on a substrate and cured to form a crosslinked coating.

4 Claims, No Drawings

CARBAMATE FUNCTIONAL OLIGOMERS AND COATINGS THEREFROM

RELATED APPLICATIONS

This application claims the benefit of provisional application, Ser. No. 60/173,557, filed Dec. 30, 1999, the disclosure thereof being incorporated herein in its entirety.

BACKGROUND OF THE INVENTION

The synthesis of 2-hydroxy alkyl carbamates from cyclic carbonates and ammonia or primary amines is well known to those skilled in the art. U.S. Pat. No. 5,912,382 discloses a process for the preparation of 2-hydroxy alkyl carbamates from either propylene carbonate or butylene carbonate and ammonia using an active hydroxyl compound as an initiator for the reaction.

No prior art can be found for 2-hydroxy alkyl carbamates containing unsaturated side chains.

Carbamate functional polymers and oligomers and methods to prepare carbamate functional materials are disclosed in the literature in numerous patents.

In U.S. Pat. No. 5,336,566, carbamate functional oligomers are described which are prepared from the reaction of hydroxy propyl carbamate and a triisocyanaurate of isophorone diisocyanate. A coating was prepared by crosslinking this oligomer with an aminoplast resin. This reference discloses that carbamate functional oligomers or polymers can be prepared from the reaction of any hydroxy carbamate with an oligomer or polymer containing isocyanate groups. The synthetic route to the hydroxy carbamate is not disclosed. The drawing included in the patent indicates that the synthetic route taken results in 1,3-hydroxypropyl carbamate. Also, while the possible use of other carbamates, such as hydroxy butyl carbamate, is mentioned, the effect of changing the structure of the carbamate on the properties of the oligomer or the coating is not disclosed.

U.S. Pat. Nos. 5,300,328; 5,356,669; 5,474,811; 5,605,965; 5,726,246 and EP 594,142 disclose the preparation of a carbamate functional polymer from the reaction of hydroxy propyl carbamate with an isocyanate functional polymer.

U.S. Pat. Nos. 5,373,069; 5,512,639 and 5,719,237 disclose the preparation of a carbamate functional oligomer from the reaction of hydroxy propyl carbamate and a difunctional isocyanate or the adduct of a difunctional isocyanate with a polyol.

U.S. Pat. Nos. 5,792,810 and EP 767,231 disclose the reaction of hydroxy propyl carbamate with caprolactone to form an adduct that retains both carbamate and hydroxyl functionality.

U.S. Pat. Nos. 5,792,810; 5,770,650; 5,760,127; and EP 869,139 and 767.187 disclose the preparation of carbamate functional polymer from the reaction of hydroxy propyl carbamate with caprolactone, followed by the reaction of the adduct with either a diisocyanate or adduct of a diisocyanate with a polyol. The use of caprolactone helps reduce the viscosity of the carbamate functional oligomer so that higher solids coatings can be prepared.

Several other patents disclose other methods of preparing oligomers or polymers with carbamate functionality. U.S. Pat. No. 5,766,769 discloses reacting hydroxy propyl carbamate with the cyclic siloxane, tetramethyl cyclotetrasiloxane. U.S. Pat. No. 5,756,213 discloses reacting a hydroxy propyl carbamate—caprolactone adduct with a carbonate to prepare a difunctional carbamate functional oligomer. Similarly, EP 767,226 discloses reacting a hydroxy propyl carbamate—caprolactone adduct with urea to form a difunctional carbamate functional oligomer.

To provide a water reducible carbamate functional oligomer, EP 661,315 discloses the reaction of a trifunctional IPDI adduct with dimethylolproprionic adduct and hydroxy propyl carbamate.

SUMMARY OF THE INVENTION

Carbamate functional oligomers are disclosed which are the reaction product of a hydroxy carbamate having pendant alkyl or vinyl groups and an oligomer or polymer containing at least one isocyanate group.

DETAILED DESCRIPTION

Hydroxy carbamates useful in this invention are most conveniently prepared from the reaction of a cyclic carbonate and either ammonia or a primary amine. Thus, ammonia can be reacted with ethylene carbonate to form hydroxy ethyl carbamate. When ammonia is reacted with propylene carbonate, 2-hydroxy propyl carbamate ((methyl)-2-hydroxy ethyl carbamate) is formed.

In this invention, ammonia or a primary amine is reacted with a cyclic carbonate having a pendant alkyl group of greater than one carbon atom. Thus, ammonia can be reacted with butylene carbonate, pentylene carbonate, hexylene carbonate to yield 2-hydroxy ethyl carbamates having ethyl, propyl, and butyl pendant alkyl chains, respectively. In addition, cyclic carbonates containing unsaturated side chains can be used. Thus, 4-vinyl ethylene carbonate can be reacted with ammonia to afford (vinyl)-2-hydroxy ethyl carbamate.

The carbamate functional oligomers of this invention are prepared by reacting a hydroxy carbamate with any polymer or oligomer having groups that are reactive with the hydroxyl group and not the carbamate group.

More preferred are monomers, polymers or oligomers having isocyanate groups.

Typical isocyanate compounds that may be useful for this invention are diisocyanates such as toluene diisocyanate, isophorone diisocyanate, hexamethylene diisocyanate, methylene diphenyl diisocyanate [MDI], α,α,α',α'-xylylene diisocyanate [TMXDI], and the like.

More preferred are oligomers prepared from the controlled polymerization or oligomerization of the difunctional isocyanates listed above. For example, oligomers of hexamethylene diisocyanate are sold under the tradename Desmodur by Bayer. The triisocyanarate of isophorone diisocyanate is sold as T1890 by Huls.

Also preferred are adducts made from reaction of a diisocyanate with a trifunctional alcohol. For example, three moles of a diisocyanate such as TMXDI can be reacted with one mole of trimethylol propane to yield an isocyanate functional oligomer.

Also useful for this invention are isocyanate functional polymers prepared from the free-radical polymerization of a vinyl monomer containing an isocyanate group. Such isocyanate functional vinyl monomers include m-isopropenyl-α,α-dimethyl benzyl isocyanate [m-TMI], isocyanatoethyl methacrylate, and the reaction product of a hydroxy functional vinyl monomer (such as hydroxy ethyl acrylate) with a diisocyanate.

The reaction of the hydroxy alkyl carbamate with the isocyanate functional oligomer or polymer may be conducted either in the presence or in absence of solvent. It is important that any solvent used not be reactive with the isocyanate. Solvents which can be used are toluene, xylene, esters such as butyl acetate, propylene glycol methyl ether acetate, EEP, ketones such as acetone methyl amyl ketone, and the like.

The reaction of the hydroxy alkyl carbamate with the isocyanate functional oligomer or polymer can also be conducted at ambient or elevated temperatures and, optionally, in the presence of a catalyst. Typical catalysts are those known in the art for catalyzing the reaction of an isocyanate with an alcohol. Preferred are tin compounds.

We have found that using hydroxy alkyl carbamates with pendant alkyl groups of greater than one carbon atom result in carbamate functional oligomers having lower solution viscosity than those with pendant alkyl chains with one or less carbon atoms. Considering the large amount of prior art in this area, the fact that using 2-hydroxy carbamates with pendant alkyl chains of greater than one carbon atom has not been disclosed as a way to reduce viscosity of the carbamate functional oligomer indicates that this invention is not obvious. Reducing the viscosity of carbamate functional oligomers is important in preparing higher solids coatings.

The carbamate functional polymer or oligomer is mixed with an aminoplast resin and optionally, pigments, flow control additives, rheology additives, catalysts, and solvents, to form a mixture that can be applied to a substrate and cured to form a coating. The aminoplast resin can be any etherified and alkylated resin derived from melamine or urea and formaldehyde.

In the following examples, several materials will be identified by abbreviations or trade names. These are identified as follows:

T1890-100 is a 100% solids version of the triisocyanaurate of isophorone diisocyanate from Huls.

PM acetate is the acetate of propylene glycol monomethyl ether.

DBTDL is dibutyl tin dilaurate.

Resimene 745 (R-745) is substantially hexamethoxy methyl melamine resin supplied by Solutia, Inc. (formerly Monsanto).

FC-430 is a fluorocarbon flow aid from 3M.

PTSA is p-toluene sulfonic acid.

The polymers and coatings are characterized using the following methods:

Fourier Transform Infrared Spectroscopy

Fourier Transform Infrared Spectroscopy is used to follow the reaction of the hydroxy carbamate with isocyanate. Samples were coated onto zinc selenide crystals and a FTIR spectrum measured.

Methyl Ethyl Ketone Resistance

Cured films were rubbed with a methyl ethyl ketone saturated cloth according to ASTM D-5402. Results are reported as the number of double rubs required for breakthrough of the film to the substrate. Test is terminated after 300 MEK double rubs. A rating of >300 indicates that the film was not marred.

Pencil Hardness

Pencil hardness was measured using a series of pencils containing leads of differing hardness according to ASTM D-3363. The hardness is reported as the hardest pencil lead that does not penetrate the coating film.

Konig Pendulum Hardness

The Konig pendulum hardness (KPH) is determined using a Byk-Gardner pendulum hardness tester according to ASTM D-4366. Hardness is reported as the number of seconds required for the pendulum swing to be damped from a 6° swing to a 3° swing.

Impact Resistance

Forward and reverse impact resistance is determined using a falling dart impact tester according to ASTM D-2794. Results are reported as the maximum in-lbs of force where the film remains intact.

COMPARATIVE EXAMPLE 1

In a 1-liter, 3-neck, round bottom flask equipped with a magnetic stirrer, temperature probe, gas dispersion tube, and condenser was placed propylene carbonate (450 ml) and methanol (40 ml). Ammonia gas was bubbled into the reaction mixture. Reaction was run until the reaction was 90.4% product as determined by Gas Chromatography. Product was purified by wiped film distillation at 140° C. and 5mm Hg resulting in 96.8% pure 2-hydroxy propyl carbamate (mixture of two isomers).

EXAMPLE 2

Into a 500 ml, 3-neck, round bottom flask equipped with a condenser, magnetic stirrer, temperature probe and gas dispersion tube was placed 4-vinyl ethylene carbonate (300 ml) and methanol (100 ml). Ammonia was bubbled into the reaction while keeping the reaction temperature below 26° C. with the help of an ice bath. Ammonia addition discontinued overnight. Reaction was found to be 94.5% after stirring overnight. Placed still head on reaction and heated to 80° C. and 2 mm Hg vacuum to remove any low boiling materials. Distillation continued with three fractions taken. Majority of the material was collected and found to be 95.8% pure 2-hydroxy butenyl carbamate (mixture of two isomers).

EXAMPLE 3

Into a 500 ml, 3-neck, round bottom equipped with a magnetic stirrer, temperature probe., condenser, and gas dispersion tube was placed butylene carbonate (300 ml) and methanol (100 ml). Reaction placed in an ice bath to keep the reaction temperature below 26° C. during the bubbling of the ammonia into the reaction. Reaction was stirred overnight but the ammonia addition was stopped then restarted the next morning. The reaction was placed on a rotary evaporator at ~250 mm Hg and 40° C. to remove any low boiling materials. Material solidified, upon cooling, to a waxy, orange material. Sample was filtered and washed with heptane. Product was recrystalized in acetone/heptane mixture. The crystals were collected and washed with heptane. Two sets of crystals were collected which were 98.0 and 96.2% pure 2-hydroxy butyl carbamate (mixture of two isomers).

COMPARATIVE EXAMPLE 4

Into a 250 mL, 3-neck, round bottom flask equipped with a temperature probe, nitrogen inlet, condenser, heating mantle and magnetic stirrer was placed T-1890-100 (43.99g, 0.06 mol) dissolved in 20.07 g PM acetate. To this was added a solution consisting of 2-hydroxy propyl carbamate (21.44 g, 0.18 mol, Comparative Example 1)) dissolved in 18.99 g PM acetate. DBTDL (0.24 g 95%) and n-butanol (1.42 g) were added to the reaction mixture. Reaction heated to 80° C. and maintained for ~6 hours until FTIR of reaction showed no residual isocyanate.

EXAMPLE 5

Into a 250 ml, 3-neck, round bottom flask equipped with a temperature probe, nitrogen inlet, condenser, heating mantle and magnetic stirrer was placed T-1890-100 (43.99 g, 0.06 mol) dissolved in 22.10 g PM acetate. To this was added a solution consisting of 2-hydroxy butenyl carbamate (23.61 g, 0.18 mol, Example 2) dissolved in 20.92 g PM acetate. DBTDL (0.26 g, 95%) and n-butanol (1.56 g) were added to the reaction mixture. Reaction heated to 80° C. and maintained for ~6 hours until FTIR of reaction showed no residual isocyanate.

EXAMPLE 6

Into a 250 mL, 3-neck, round bottom flask equipped with a temperature probe, nitrogen inlet, condenser, heating mantle and magnetic stirrer was placed T-1890-100 (43.93 g, 0.06 mol) dissolved in 22.44 g PM acetate. To this was added a solution consisting of 2-hydroxy butyl carbamate (23.97 g, 0.18 mol, Example 3) dissolved in 21.24 g PM acetate. DBTDL (0.27 g, 95%) and n-butanol (1.58 g) were added to the reaction mixture. Reaction heated to 80° C. and maintained for ~6 hours until FTIR of reaction showed no residual isocyanate.

EXAMPLE 7

Percent solids was determined for the resins in Examples 4 through 6 reactions, then adjusted to 55% using PM acetate. Viscosity data (in cps at 55% solids) determined using a Brookfield RV viscometer (#7 spindle) as follows:

TABLE 1

Viscosity of Resin Solutions.

| Example | 5 rpm | 10 rpm |
|---|---|---|
| 4 | 21750 | 21630 |
| 5 | 21300 | 21180 |
| 6 | 18600 | 18450 |

These results indicate that using the carbamates with higher alkyl groups reduce the solution viscosity of the urethane carbamate.

EXAMPLE 8

Coating formulations were prepared according to the following table. The solvent blend used is a mixture of xylenes/methyl n-amyl ketone/ethyl ethoxy propionate/n-butanol (55/32/6.5/6.5). Panels baked at 160° C. for 30 minutes.

TABLE 2

Coatings Formulations.

| Resin from Example | Resin | R-745 | Solvent Blend | FC-430 (30% MAK solution) | PTSA (30% isopropanol solution) |
|---|---|---|---|---|---|
| 4 | 9.00 | 2.31 | 1.44 | 0.10 | 0.08 |
| 5 | 9.01 | 2.26 | 1.19 | 0.10 | 0.08 |
| 6 | 9.00 | 2.25 | 1.16 | 0.10 | 0.07 |

TABLE 3

Coatings Properties.

| Resin from Example | KPH (sec) | P.H. (cut) | MEK (double rubs) | Impact, in-lbs (F/R) |
|---|---|---|---|---|
| 4 | 198 | 3 H | 300 | 30/<6 |
| 5 | 190 | 3 H | 300 | 27/<6 |
| 6 | 191 | 3 H | 300 | 24/<6 |

The claimed invention is:

1. A beta-hydroxy alkenyl carbamate compound of formula I:

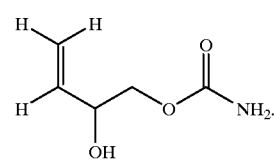

(I)

2. A carbamate functional oligomer comprising the reaction product of:

(i) a beta-hydroxy alkenyl carbamate compound of formula I:

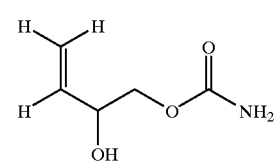

(I)

and (ii) a polyfunctional isocyanate compound.

3. A curable coating composition composed of:

a) carbamate functional oligomer of claim 2; and b) a crosslinker having carbamate-reactive functional groups.

4. A curable coating composition of claim 3, wherein the crosslinker is a melamine-formaldehyde resin.

* * * * *